(12) United States Patent
Maschke

(10) Patent No.: US 7,653,441 B2
(45) Date of Patent: Jan. 26, 2010

(54) INTRAVENOUS PACEMAKER ELECTRODE

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 631 days.

(21) Appl. No.: 11/316,063

(22) Filed: Dec. 22, 2005

(65) Prior Publication Data

US 2006/0190068 A1 Aug. 24, 2006

(30) Foreign Application Priority Data

Dec. 23, 2004 (DE) ............... 10 2004 062 398

(51) Int. Cl.
*A61N 1/00* (2006.01)

(52) U.S. Cl. ..................................... 607/128

(58) Field of Classification Search .......... 607/115–130
See application file for complete search history.

(56) References Cited

U.S. PATENT DOCUMENTS

| | | | |
|---|---|---|---|
| 4,162,679 A | | 7/1979 | Reenstierna |
| 4,258,724 A | * | 3/1981 | Balat et al. .................. 607/128 |
| 4,280,512 A | | 7/1981 | Karr et al. |
| 4,809,713 A | | 3/1989 | Grayzel |
| 4,957,118 A | * | 9/1990 | Erlebacher .................. 607/128 |
| 5,505,730 A | * | 4/1996 | Edwards ...................... 606/41 |
| 5,800,497 A | * | 9/1998 | Bakels et al. ................. 607/122 |
| 5,871,507 A | | 2/1999 | Obel et al. |
| 6,241,671 B1 | | 6/2001 | Ritter et al. |
| 6,330,467 B1 | | 12/2001 | Creighton, IV et al. |
| 6,772,001 B2 | | 8/2004 | Maschke |
| 7,008,418 B2 | * | 3/2006 | Hall et al. ...................... 606/41 |
| 2002/0019644 A1 | | 2/2002 | Hastings et al. |
| 2003/0144590 A1 | | 7/2003 | Maschke |
| 2003/0176786 A1 | | 9/2003 | Maschke |
| 2004/0158142 A1 | | 8/2004 | Hall et al. |

FOREIGN PATENT DOCUMENTS

| | | |
|---|---|---|
| DE | 28 43 096 A1 | 4/1980 |
| DE | 33 00 050 C2 | 7/1984 |
| DE | 41 12 936 A1 | 10/1991 |
| DE | 698 07 986 T2 | 12/1998 |
| DE | 102 03 372 A1 | 9/2003 |

OTHER PUBLICATIONS

"Herzschrittmacher—Elektrode", Herzschrittmacherelektrode: Stand der Technik/1, http://www.biotronik.com, Mar. 7, 2004, pp. 1-6, Siemens AG Medical Solutions.
G. Sabin, M. Bergbauer, "Herz-schrittmacher", Reihe Kardiologie, pp. 55-58, Aktuelles Wissen Hoechst.
L. Binner, V. Hombach, "Technik der Herzschrittmachertherapie", Interventionelle Kardiologie, Angiologie und Kardiovaskularchirurgie, pp. 165-177, Chapter 9, Schattauer Verlag Stuttgart.

* cited by examiner

Primary Examiner—George Manuel
Assistant Examiner—Shubatra Narayanaswamy

(57) ABSTRACT

An intravenous pacemaker electrode comprises an electrode tip provided for transmission of stimulation pulses to the heart as well as at least one fixing element provided for fixing the electrode tip to the heart, of which the form and/or arrangement can be changed relative to the electrode tip, as well as a suitable actuation element for magnetic actuation of the fixing element.

10 Claims, 2 Drawing Sheets

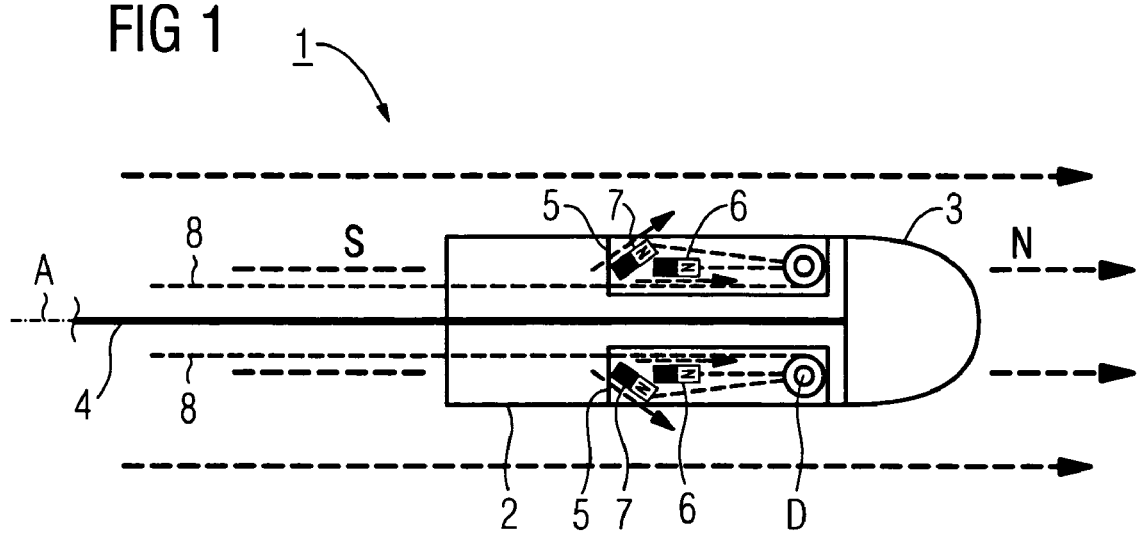
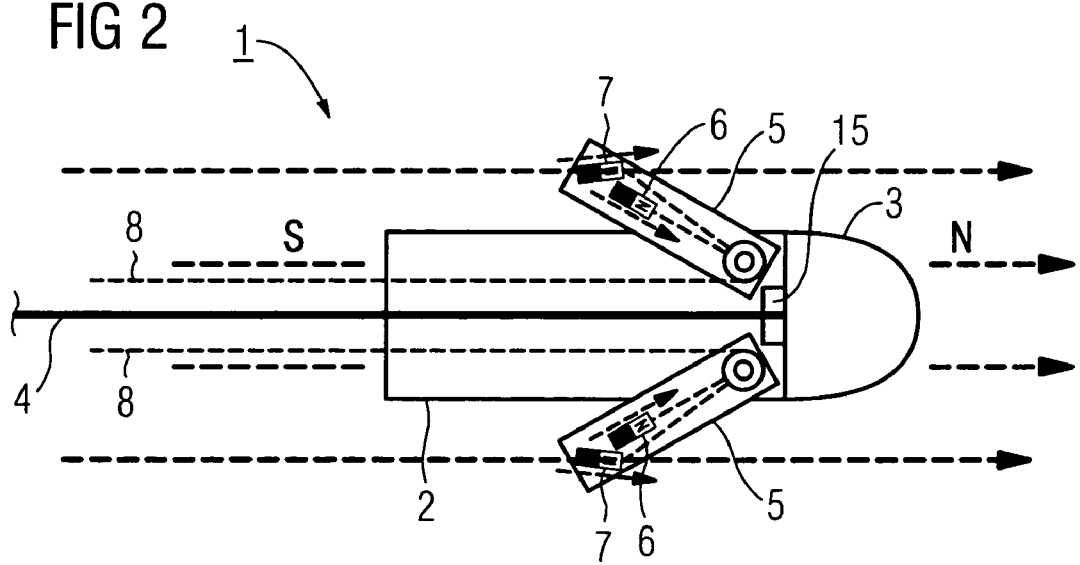

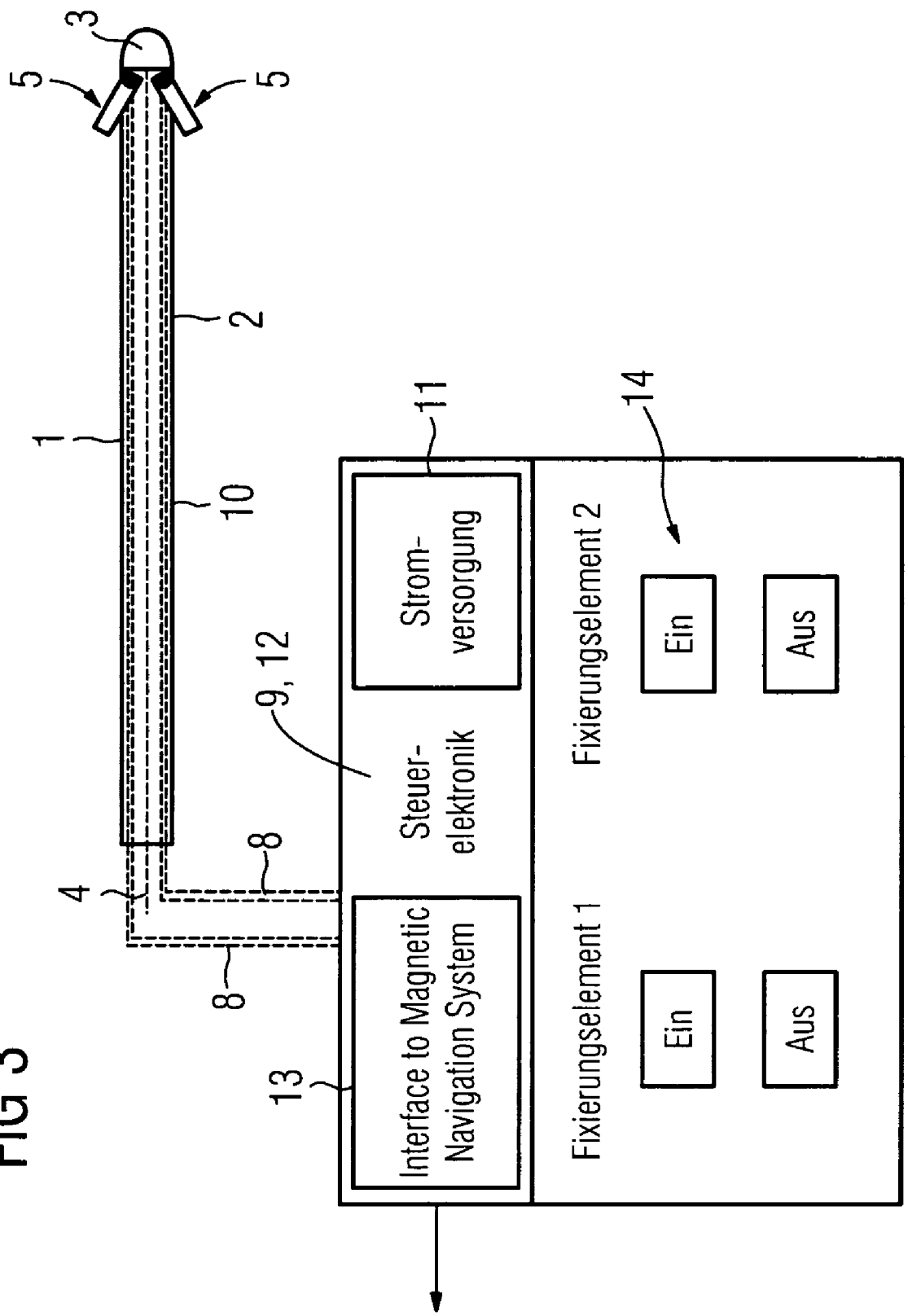

INTRAVENOUS PACEMAKER ELECTRODE

CROSS REFERENCE TO RELATED APPLICATION

This application claims priority of the German application No. 10 2004 062 398.8 DE filed Dec. 23, 2004, which is incorporated by reference herein in its entirety.

FIELD OF THE INVENTION

The invention relates to implantable, intravenous pacemaker electrode with an electrode tip provided for transmission of stimulation pulses as well as at least one fixing element with geometry that can be changed relative to the electrode tip, which is provided for fixing the electrode tip to the heart.

BACKGROUND OF THE INVENTION

A pacemaker electrode of this type is known for example from DE 33 00 050 C2.

The pacemaker electrode disclosed in DE 33 00 050 C2 features as its fixing elements bands or threads which, on implantation of the pacemaker electrode, lie close to its surface. That section of the electrode cable of the pacemaker to which the bands or threads are attached at their ends can be compressed slightly with a mandrin running through the electrode cable. This compression makes the bands or threads stand out from the pacemaker electrode in an arc shape and they is thus intended to develop their effect as fixing elements. A renewed movement of the mandrin in the opposite direction is designed to stretch the bands or threads again so that a change in position of the electrode tip is possible.

U.S. Pat. No. 4,280,512 discloses a pacemaker electrode with a fixing element which, by contrast with the fixing element known from DE 33 00 050 C2, features free ends which are intended to be able to penetrate into the tissue of the heart. In this case an activation and also a deactivation of the fixing element is to be possible, with a mandrin that can be moved within the electrode cable also being provided for this purpose here. To deactivate the fixing element, i.e. to fold in the free ends of the fixing element, a hook-shaped part of the mandrin is to be hooked into an eye-shaped part of the fixing element. However this process might be difficult to perform with implantable pacemaker electrodes.

Implantable pacemaker electrodes in accordance with the prior art can barely be removed again once implanted. If a new pacemaker electrode is to be implanted, the unusable electrode cable is thus cut off as a rule, so that the old electrode tip remains implanted. This can lead to complications, especially inflammations or to a perforation of the heart chamber because of the electrode left in it.

SUMMARY OF THE INVENTION

The object of the invention is to specify a pacemaker electrode with an electrode tip which is also especially suitable for de-implantation.

In accordance with the invention this object is achieved by an intravenous pacemaker electrode with the features of the claims. This pacemaker electrode features an electrode tip provided for transmission of stimulation pulses to the heart as well as at least one fixing element for attaching the electrode tip to the heart. The fixing element has an inherently variable geometry and/or is arranged so that it's position can be altered relative to the electrode tip. It is possible to actuate the fixing element by magnetic force. An actuation element provided for this purpose is in the simplest case a ferrous part which can be influenced by a magnetic field. Preferably however a magnet, especially an electromagnet, is used as actuation element. This magnet can be influenced by an external magnetic field, as is principally known for example from U.S. Pat. No. 6,241, 671 B1, U.S. Pat. No. 6,330,467 B1 or US 2003/0144590 A1. Especially advantageous is the option of also being able to vary the magnetic field created by an electromagnet in the pacemaker electrode when the pacemaker electrode is implanted, as is known in principal for example from US 2003/0176786 A1.

The actuation element provided for reversible activation and deactivation of the fixing element is preferably arranged within this actuation element, can however also be arranged in any way at another location in the pacemaker electrode and linked mechanically to the fixing element. The fixing element preferably features at least one free end which can penetrate into the myocardium as a kind of anchor.

In a preferred embodiment one at least approximately inherently rigid fixing element is supported relative to the electrode tip so that it can swivel on this or on a part mechanically connected to it. Preferably the pacemaker electrode features at least two fixing elements which are arranged symmetrically to an axis of symmetry running along the pacemaker electrode through the electrode tip.

The at least one fixing element is preferably supported sprung on the electrode tip or on a part mechanically connected to the tip. The sprung support can in this case be embodied such that the fixing element is in the folded-out or extended position, i.e. the active position, while no magnetic force is being exerted on the fixing element. In this case the fixing element must be moved during implantation of the pacemaker electrode by a force created with the aid of an external magnetic field into the passive, i.e. folded-in or withdrawn position. The external magnetic field will thus be needed during the entire implantation process, until such time as the electrode tip has reached its intended position at the heart.

Alternatively it is also possible the support the fixing element so that it is sprung in a bistable state, so that it can be held without the external magnetic field both in the active position and also in the passive position through spring force. The variant of the sprung support of the fixing element has the advantage that the external magnetic field will only be needed at the time or activation or deactivation of the fixing element.

In accordance with an advantageous embodiment, a number of actuation elements, especially magnets, are arranged for actuation of a specific fixing element, especially within the fixing element. The individual actuation elements of the fixing element can in this case be embodied to be similar or different.

In this embodiment, as in all others, combinations of ferrous parts, permanent magnets and electromagnets can also be provided as actuation elements. The plurality of actuation elements per fixing element has the advantage that the individual actuation elements can be assigned different functions. For example one actuation element can serve merely to fold out the fixing element and another actuation element merely to fold it in. Likewise a first actuation element can be provided to block a specific positioning of the fixing element or to cancel the blocking while a second actuation element changes the fixing element from the active to the passive state or vice versa.

Where the at least one actuation element needs a power supply, this runs through the electrode cable of the pacemaker electrode. A simultaneous transmission of stimulation pulses to the electrode tip and actuation of the fixing element or fixing elements is not required. For this reason it is possible to use the same lead to supply power to the actuation element as is also used for transmission of the stimulation pulses to the electrode tip. A suitable switching element can if necessary be arranged in the electrode tip or in a section of the electrode cable adjoining the electrode tip.

With the aid of an external magnetic field it is not only possible, with the aid of a preferred development, to activate or deactivate the fixing element, but also to navigate the electrode tip overall in the body of the patient. A part within the pacemaker electrode allowing controlled movement of the pacemaker electrode can in this case be identical overall to a component of the actuation element of the fixing element or with the actuation element overall. As regards the basic option of magnetic navigation of a medical product in the body of a patient, the reader is referred to the above-mentioned US 2003/0176786 A1 as well as to US 2002/0019644 A1.

The advantage of the invention lies especially in the fact that movably supported fixing elements on the electrode tip of a pacemaker electrode can be reversibly activated or deactivated with the aid of an external magnetic field, so that the pacemaker electrode including electrode tip can if necessary be de-implanted especially simply and with low risk.

BRIEF DESCRIPTION OF THE DRAWINGS

An exemplary embodiment of the invention is explained in more detail below with reference to a drawing. The figures show schematic diagrams of:

FIGS. 1,2 sections of a pacemaker electrode with magnetically actuatable fixing elements, and FIG. 3 a pacemaker electrode connected to an operating unit with magnetically actuatable fixing elements.

DETAILED DESCRIPTION OF THE INVENTION

Parts and parameters which correspond to each other are always shown by the same reference symbols in all the figures.

FIGS. 1,2 show an outline schematic of a pacemaker electrode 1 in cross section with an electrode cable 2 and an electrode tip 3, which is essentially made of a conductive material, such a carbon, platinum or titanium and serves to transmit stimulation pulses to a myocardium not shown in the diagram. The pacemaker electrode 1 can be just as much part of a unipolar pacemaker system as of a bipolar pacemaker system. Independently of this the pacemaker electrode 1 can be used not only for transmission of electrical pulses to the heart but also for detection of electrical signals of the heart, i.e. for what is known as sensing. The pacemaker electrode 1 can be attached either in the atrium or in the ventricle.

The stimulation pulses are transmitted to the electrode tip 3 by means of a lead 4, which in the exemplary embodiment runs through center of the electrode cable 2. As an alternate a non-central arrangement of lead 4 in the electrode cable 2 is also possible. The position of lead 4 shown in the diagram corresponds to an axis of symmetry which runs through the electrode tip 3. Adjacent to the electrode tip 3 are two fixing elements 5 which can each be swiveled in the form of a folding anchor around a pivot point D. The positions of the pivot points D cannot be changed relative to the electrode tip, and by contrast with how they are presented in the drawing, can also be located directly at the electrode tip 3.

The inherently at least essentially rigid fixing elements 5, which serve to fix the electrode tip 3 at the myocardium are supported sprung in a manner not presented in any greater detail, for example by means of rotary springs at the pivot points D and arranged symmetrically to the axis of symmetry A. Instead of two fixing elements 5, the pacemaker electrode 1 can also feature a larger number, for example three or four, fixing elements 5 in a way not shown, which are preferably distributed in a similar form around the circumference of the electrode tip 3. In each case the fixing elements 5 are designed so as not to obstruct the introduction of the pacemaker electrode 1 into a vein of the patient.

The position of the fixing elements 5 shown in FIG. 1 is designated as the passive or deactivated position, the unfolded position of the fixing elements shown in FIG. 2 as their active position To move the fixing elements 5 from their passive into their active position each one of the fixing elements 5 features two actuation elements 6,7. These actuation elements 6,7, which are completely integrated into the flap-shaped fixing elements 5, are electromagnets, to which power can be supplied by means of connecting lines 8, which run parallel to line 4 in the electrode cable 2.

In the exemplary embodiment the pacemaker electrode 1 is subjected to an external magnetic field which is indicated by the dashed arrows and aligned in parallel to the axis of symmetry A. The two actuation elements 6,7 in the fixing elements 5 have a different orientation to the axis of symmetry A. In the folded-in state of the fixing elements 5 (FIG. 1) the first actuation element 6 is aligned in parallel to the axis of symmetry A, while the second actuation element 7 forms an angle of around 20° to 45° with this. To reliably prevent any accidental unfolding of the fixing elements 5 during implantation the fixing elements 5 are initially mechanically blocked in the position shown in FIG. 1. To cancel this blocking, when the electrode tip 3 has reached its final position at the myocardium, the first actuation element 6 is activated, which essentially exerts on the fixing element 5 a force in the direction of the axis of symmetry A. The subsequent unfolding of the fixing element 5 into the position shown in FIG. 2 occurs with the aid of the second actuation element 7, which in the folded-out state of the fixing element 5 is aligned in parallel to the axis of symmetry S. The sprung support of the fixing elements 5 is designed in the exemplary embodiment such that the fixing elements 5 are in a stable position both in the position shown in FIG. 1 and also in the position shown in FIG. 2. The external magnetic field which is needed for the actuation of the fixing elements 5 and typically exhibits a field strength of around 500 mT (0.5 Tesla) on the surface of a the patient's body and 80 mT at the electrode, is thus not yet needed when the pacemaker electrode 1 is being pushed forward through the vein of the patient.

For the de-implantation of the pacemaker electrode 1 the processes explained above are performed in the reverse order, i.e. the fixing elements 5 are initially folded in at the pacemaker electrode 1 so that this can be removed. With the aid of the external magnetic field not only the fixing elements 5, but also the electrode tip 3 can be move as a whole. For this purpose a further, symbolically shown magnet element 15 is arranged in or at the electrode tip 3.

FIG. 3 shows a control unit 9 to which a pacemaker electrode 1 is connected, which is embodied in a similar way to the exemplary embodiment in accordance with FIG. 1 and 2. A sleeve 10 of the electrode cable 2 is connected liquid-tight to the electrode tip 3, which functions as a cathode. The pacemaker electrode 1 shown in FIG. 3 is part of a unipolar pacemaker system, in which a pacemaker housing not shown acts as an anode. Similarly the system could however also be embodied as a bipolar system in which a special anode is spaced from the electrode tip 3 by around 2-3 cm. Especially in the case of sensing by means of the pacemaker electrode 1, a low-resistance coupling of the electrode tip 3 at the myocardium, to which the stable retention with the aid of the fixing elements 5 makes a major contribution, is of great importance.

The control unit 9, in addition to a power supply 11 and control electronics 12, also features a connection module 13, which is provided for communication with a magnetic navigation system. The individual fixing elements 5 are able to be actuated separately in the exemplary embodiment in accordance with FIG. 3 by means of operating keys 14. Unlike in this exemplary embodiment it is also possible to always control the fixing elements 5 simultaneously and/or use the line 4 for activation of the fixing elements 5.

The invention claimed is:

1. An intravenous pacemaker electrode, comprising:
   an electrode tip configured to transmit stimulation pulses to a patients heart on an ongoing basis;
   a selectively actuated fixing element arranged at the electrode tip and configured to:
     secure the electrode tip to the heart on an ongoing basis having a form and/or an arrangement that is changed relative to the electrode tip, and
     deactivate without damage to a patients heart; and
   an actuation element suitable for magnetic actuation of the fixing element.

2. The pacemaker electrode in accordance with claim 1, wherein a magnet is provided as the actuation element.

3. The pacemaker electrode in accordance with claim 2, wherein an electromagnet is provided as the actuation element.

4. The pacemaker electrode in accordance with claim 1, wherein the actuation element is arranged in the fixing element.

5. The pacemaker electrode in accordance with claim 4, wherein a plurality of actuation elements are arranged within the fixing element.

6. The pacemaker electrode in accordance with claim 1, wherein the actuation element is supported so that it can swivel relative to the electrode tip.

7. The pacemaker electrode in accordance with claim 6, wherein the actuation element has a spring support.

8. The pacemaker electrode in accordance with claim 1, wherein a plurality of actuation elements are arranged symmetrically to an axis of symmetry extending through the electrode tip.

9. The pacemaker electrode in accordance with claim 1, wherein a line used for transmission of stimulation pulses to the electrode tip is also a power feed to the actuation element.

10. The pacemaker electrode in accordance with claim 1, wherein a magnetic element coupled mechanically to the electrode tip produces magnetic navigation.

* * * * *

UNITED STATES PATENT AND TRADEMARK OFFICE
CERTIFICATE OF CORRECTION

PATENT NO. : 7,653,441 B2 Page 1 of 1
APPLICATION NO. : 11/316063
DATED : January 26, 2010
INVENTOR(S) : Michael Maschke It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1031 days.

Signed and Sealed this

Twenty-third Day of November, 2010

David J. Kappos
*Director of the United States Patent and Trademark Office*